United States Patent
Christianson et al.

(10) Patent No.: US 7,426,799 B2
(45) Date of Patent: Sep. 23, 2008

(54) AIR FRESHENER WITH FRAME AND REFILL HOLDER

(75) Inventors: Jeffrey J. Christianson, Oak Creek, WI (US); Marissa A. K. Schultz, Racine, WI (US); Stephen B. Leonard, Franksville, WI (US); Stacey L. Forkner, Waterford, WI (US); Heather R. Schramm, Whitewater, WI (US); Kara L. Lakatos, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 154 days.

(21) Appl. No.: 11/337,277

(22) Filed: Jan. 23, 2006

(65) Prior Publication Data
US 2006/0118583 A1    Jun. 8, 2006

Related U.S. Application Data

(63) Continuation-in-part of application No. 11/118,500, filed on Apr. 29, 2005, and a continuation-in-part of application No. 10/881,816, filed on Jun. 30, 2004, now Pat. No. 7,213,770, and a continuation-in-part of application No. 10/880,885, filed on Jun. 30, 2004.

(51) Int. Cl.
*A47G 1/06* (2006.01)
(52) U.S. Cl. ............................ 40/725; 40/406; 40/407; 239/55; 239/57; 239/60; 428/905
(58) Field of Classification Search .................. 40/406, 40/407, 725, 737, 765, 781, 649, 661, 600; 239/55, 60, 57, 34; 428/905
See application file for complete search history.

(56) References Cited

U.S. PATENT DOCUMENTS

| 882,710 | A | 3/1908 | Pearsall |
| 886,840 | A | 5/1908 | Mueller |
| 1,068,621 | A | 7/1913 | Abraham |
| 1,204,934 | A | 11/1916 | Burford et al. |

(Continued)

FOREIGN PATENT DOCUMENTS

EP      0 645 081      7/2001

(Continued)

OTHER PUBLICATIONS http://www.glade.com/piso.asp.

(Continued)

*Primary Examiner*—Lesley D. Morris
*Assistant Examiner*—Shin Kim

(57) ABSTRACT

A display frame with a refill holder comprises a transparent block with front and rear faces. A U-shaped mounting member is attached to the rear face about an outer periphery of same. The U-shaped mounting member has an inwardly extending wall. A channel is formed in a space between the rear face and the inwardly extending wall. A protrusion is attached to the rear face of the frame, wherein the protrusion in combination with the inwardly extending wall are configured to distance the rear face from a support surface when the frame is in a substantially horizontal position and provide a substantially unimpeded air passage adjacent the rear face.

20 Claims, 6 Drawing Sheets

U.S. PATENT DOCUMENTS

| | | | |
|---|---|---|---|
| 1,261,133 A | 4/1918 | Kidd | |
| 1,802,999 A | 4/1931 | Budd | |
| 1,815,841 A * | 7/1931 | Torsten | 40/766 |
| 1,940,328 A | 12/1933 | Schrotenboer | |
| 2,268,529 A | 12/1941 | Stiles | |
| 2,469,656 A | 5/1949 | Lienert | |
| 2,550,954 A | 5/1951 | Benedict | |
| 2,577,320 A | 12/1951 | Fenyo | |
| 2,579,715 A | 12/1951 | Wilson et al. | |
| D169,871 S | 6/1953 | Speer et al. | |
| 2,779,624 A | 1/1957 | Friedman | |
| 2,840,689 A | 6/1958 | Kazor | |
| 3,178,844 A | 4/1965 | Christian | |
| 3,424,380 A * | 1/1969 | Curran | 239/60 |
| 3,540,146 A | 11/1970 | Watkins | |
| 3,558,055 A | 1/1971 | Storchheim | |
| 3,570,160 A | 3/1971 | Spertus | |
| 3,741,711 A | 6/1973 | Bryant | |
| 3,790,081 A | 2/1974 | Thornton et al. | |
| 3,804,330 A | 4/1974 | Miller, Jr. et al. | |
| 3,822,495 A | 7/1974 | Ohfuji | |
| 3,948,445 A | 4/1976 | Andeweg | |
| D243,402 S | 2/1977 | Irving | |
| 4,009,384 A | 2/1977 | Holland | |
| D247,573 S | 3/1978 | Schimanski | |
| 4,101,720 A | 7/1978 | Taylor et al. | |
| 4,157,787 A | 6/1979 | Schwartz | |
| 4,158,440 A | 6/1979 | Sullivan et al. | |
| 4,161,283 A | 7/1979 | Hyman | |
| 4,165,573 A | 8/1979 | Richards | |
| 4,170,080 A | 10/1979 | Bergh et al. | |
| 4,173,604 A | 11/1979 | Dimacopoulos | |
| 4,184,099 A | 1/1980 | Lindauer et al. | |
| 4,285,468 A | 8/1981 | Hyman | |
| D260,503 S | 9/1981 | Stangarone | |
| 4,293,095 A | 10/1981 | Hamilton et al. | |
| 4,314,915 A | 2/1982 | Wiegers et al. | |
| D263,334 S | 3/1982 | Schimanski | |
| 4,327,056 A | 4/1982 | Gaiser | |
| D269,838 S | 7/1983 | Altonga | |
| 4,411,829 A | 10/1983 | Schulte-Elte | |
| D271,359 S | 11/1983 | Le | |
| 4,434,306 A | 2/1984 | Kobayashi | |
| D275,223 S | 8/1984 | Marxen | |
| D275,700 S | 9/1984 | Marxen | |
| 4,476,171 A | 10/1984 | Takeuchi | |
| 4,493,011 A | 1/1985 | Spector | |
| D279,146 S | 6/1985 | McCaffrey | |
| D280,363 S | 9/1985 | Wisecup, Jr. | |
| 4,549,250 A | 10/1985 | Spector | |
| 4,580,581 A | 4/1986 | Reece et al. | |
| D288,003 S | 1/1987 | Hoyt | |
| 4,634,614 A | 1/1987 | Holzner | |
| 4,695,435 A | 9/1987 | Spector | |
| 4,714,984 A | 12/1987 | Spector | |
| 4,720,409 A | 1/1988 | Spector | |
| D296,957 S | 8/1988 | Gordon et al. | |
| 4,762,275 A | 8/1988 | Herbert et al. | |
| 4,781,895 A | 11/1988 | Spector | |
| 4,794,714 A | 1/1989 | Weisgerber | |
| 4,809,912 A | 3/1989 | Santini | |
| 4,814,212 A | 3/1989 | Spector | |
| 4,849,606 A | 7/1989 | Martens, III et al. | |
| 4,874,129 A | 10/1989 | DiSapio et al. | |
| 4,883,692 A | 11/1989 | Spector | |
| D305,703 S | 1/1990 | Wang | |
| 4,898,328 A | 2/1990 | Fox et al. | |
| 4,913,349 A | 4/1990 | Locko | |
| 4,917,301 A | 4/1990 | Munteanu | |
| 4,921,636 A | 5/1990 | Traas | |
| 4,939,858 A | 7/1990 | Dailey | |
| 4,959,087 A | 9/1990 | Kappernaros | |
| 4,993,177 A | 2/1991 | Hudson | |
| 4,995,555 A | 2/1991 | Woodruff | |
| D320,266 S | 9/1991 | Kunze | |
| 5,060,858 A | 10/1991 | Santini | |
| D325,077 S | 3/1992 | Kearnes | |
| 5,148,983 A | 9/1992 | Muniz | |
| 5,148,984 A | 9/1992 | Bryson et al. | |
| 5,163,616 A | 11/1992 | Bernarducci et al. | |
| 5,170,886 A | 12/1992 | Holzner | |
| 5,219,121 A | 6/1993 | Fox et al. | |
| 5,230,867 A | 7/1993 | Kunze et al. | |
| D339,238 S | 9/1993 | Hamilton | |
| D339,242 S | 9/1993 | Sontag et al. | |
| 5,247,745 A | 9/1993 | Valentino | |
| 5,259,555 A | 11/1993 | Kiefer | |
| 5,297,732 A | 3/1994 | Hahn | |
| D346,068 S | 4/1994 | White | |
| 5,304,358 A | 4/1994 | Hoyt et al. | |
| 5,334,361 A | 8/1994 | Rafaelides et al. | |
| 5,361,522 A * | 11/1994 | Green | 40/725 |
| 5,367,802 A | 11/1994 | Rosenberg | |
| D354,627 S | 1/1995 | Rowan | |
| 5,395,047 A | 3/1995 | Pendergrass | |
| 5,402,517 A | 3/1995 | Gillett et al. | |
| D358,037 S | 5/1995 | Monroe | |
| D360,461 S | 7/1995 | Gillespie | |
| 5,439,100 A | 8/1995 | Gordon et al. | |
| D361,896 S | 9/1995 | Bramley et al. | |
| 5,462,006 A | 10/1995 | Thiruppathi | |
| D366,107 S * | 1/1996 | Shaffer | D23/366 |
| 5,503,332 A | 4/1996 | Glenn | |
| D369,473 S | 5/1996 | Gluck | |
| 5,529,243 A | 6/1996 | Hoyt et al. | |
| D372,797 S | 8/1996 | Ilaria et al. | |
| 5,556,192 A * | 9/1996 | Wang | 362/276 |
| D374,777 S | 10/1996 | Agam | |
| D376,002 S | 11/1996 | Upson | |
| D376,420 S | 12/1996 | Rymer | |
| D376,914 S | 12/1996 | Waszkiewicz | |
| D380,822 S | 7/1997 | Decker et al. | |
| 5,647,052 A | 7/1997 | Patel et al. | |
| 5,651,942 A | 7/1997 | Christensen | |
| D383,613 S | 9/1997 | Handler | |
| D384,821 S | 10/1997 | Sugar | |
| 5,679,334 A | 10/1997 | Semoff et al. | |
| 5,711,955 A | 1/1998 | Karg | |
| 5,716,000 A | 2/1998 | Fox | |
| D392,031 S | 3/1998 | Miller | |
| D392,032 S | 3/1998 | Zaragoza et al. | |
| 5,735,460 A | 4/1998 | Eisenbraun | |
| 5,744,106 A | 4/1998 | Eagle | |
| 5,749,519 A | 5/1998 | Miller | |
| 5,749,520 A | 5/1998 | Martin et al. | |
| 5,782,409 A | 7/1998 | Paul | |
| 5,788,155 A | 8/1998 | Martin et al. | |
| 5,804,264 A | 9/1998 | Bowen | |
| D399,298 S | 10/1998 | Whitehead | |
| D401,767 S | 12/1998 | Leung | |
| 5,845,847 A | 12/1998 | Martin et al. | |
| D405,473 S | 2/1999 | Tikhonski et al. | |
| D405,961 S | 2/1999 | Stangl | |
| 5,875,968 A | 3/1999 | Miller et al. | |
| 5,885,701 A | 3/1999 | Berman et al. | |
| D407,809 S | 4/1999 | Hammond | |
| 5,899,382 A | 5/1999 | Hayes et al. | |
| 5,950,922 A * | 9/1999 | Flinn | 239/34 |
| 5,961,043 A | 10/1999 | Samuelson | |
| 5,975,427 A | 11/1999 | Harries | |
| 6,031,967 A * | 2/2000 | Flashinski et al. | 392/390 |
| D424,812 S | 5/2000 | Kacius | |
| 6,065,687 A | 5/2000 | Suzuki et al. | |
| 6,106,786 A | 8/2000 | Akahoshi | |

| | | |
|---|---|---|
| 6,109,537 A | 8/2000 | Heath |
| D431,075 S | 9/2000 | Barraclough |
| 6,112,496 A | 9/2000 | Hugus et al. |
| 6,144,801 A | 11/2000 | Lehoux et al. |
| 6,152,379 A | 11/2000 | Sorgenfrey |
| 6,154,607 A | 11/2000 | Flashinski et al. |
| D435,100 S | 12/2000 | Pesu et al. |
| D437,404 S | 2/2001 | Wu |
| 6,203,394 B1 * | 3/2001 | Lee .................. 446/159 |
| D439,964 S | 4/2001 | Wu |
| D441,441 S | 5/2001 | Upson |
| D445,262 S | 7/2001 | Rowan |
| 6,254,248 B1 | 7/2001 | McAuley et al. |
| 6,254,836 B1 | 7/2001 | Fry |
| D451,990 S | 12/2001 | Millet |
| 6,328,935 B1 | 12/2001 | Buccellato |
| D453,561 S | 2/2002 | Nelson |
| 6,354,710 B1 | 3/2002 | Nacouzi |
| 6,358,577 B1 | 3/2002 | Bowen et al. |
| 6,363,734 B1 | 4/2002 | Aoyagi |
| 6,367,706 B1 | 4/2002 | Putz |
| D456,620 S | 5/2002 | Vincent |
| D456,888 S | 5/2002 | Buthier |
| D461,006 S | 7/2002 | Buthier |
| D461,393 S | 8/2002 | Aubert |
| 6,435,423 B2 | 8/2002 | Hurry et al. |
| 6,478,440 B1 | 11/2002 | Jaworski et al. |
| 6,484,425 B1 | 11/2002 | Hirsch |
| 6,526,636 B2 | 3/2003 | Bernhardt |
| 6,548,015 B1 | 4/2003 | Stubbs et al. |
| 6,555,068 B2 | 4/2003 | Smith |
| D476,726 S | 7/2003 | Rosenberg |
| 6,610,254 B1 | 8/2003 | Furner et al. |
| D479,742 S | 9/2003 | Hollingsworth |
| 6,618,974 B2 * | 9/2003 | Szalay ................ 40/611.06 |
| 6,627,857 B1 | 9/2003 | Tanner et al. |
| D480,221 S | 10/2003 | Luciano |
| D481,113 S | 10/2003 | Groene et al. |
| 6,631,852 B1 | 10/2003 | O'Leary |
| 6,638,591 B2 | 10/2003 | Bowen et al. |
| D481,785 S | 11/2003 | Koike |
| 6,643,967 B1 | 11/2003 | Bloom |
| 6,648,239 B1 | 11/2003 | Myny et al. |
| 6,663,838 B1 | 12/2003 | Soller et al. |
| D485,607 S | 1/2004 | Wu |
| D487,308 S | 3/2004 | Engerant |
| 6,705,541 B2 | 3/2004 | Schuehrer et al. |
| 6,714,725 B2 | 3/2004 | Grone et al. |
| 6,722,578 B2 | 4/2004 | Skalitzky et al. |
| 6,730,311 B2 | 5/2004 | Maleeny et al. |
| 6,749,672 B2 * | 6/2004 | Lynn .................... 96/222 |
| 6,790,436 B2 | 9/2004 | Williams et al. |
| 6,808,791 B2 | 10/2004 | Curro et al. |
| D498,524 S | 11/2004 | Morillas |
| D498,525 S | 11/2004 | Harbutt et al. |
| D498,836 S | 11/2004 | Morillas |
| 6,826,863 B1 * | 12/2004 | Goodfellow ............. 40/725 |
| 6,998,581 B2 | 2/2006 | Currie |
| 7,028,917 B2 | 4/2006 | Buthier |
| 7,036,747 B2 | 5/2006 | Channer |
| 7,138,367 B2 | 11/2006 | Hurry et al. |
| 7,175,815 B2 | 2/2007 | Yamasaki et al. |
| 2003/0007887 A1 | 1/2003 | Roumpos et al. |
| 2003/0085297 A1 | 5/2003 | Huang |
| 2003/0089791 A1 | 5/2003 | Chen et al. |
| 2003/0094503 A1 | 5/2003 | Rymer et al. |
| 2003/0200690 A1 | 10/2003 | Galloway |
| 2004/0000596 A1 | 1/2004 | Cuthbert |
| 2004/0057975 A1 | 3/2004 | Maleeny et al. |
| 2004/0262418 A1 | 12/2004 | Smith et al. |
| 2005/0001337 A1 | 1/2005 | Pankhurst |
| 2005/0103880 A1 | 5/2005 | Taite |
| 2005/0145711 A1 | 7/2005 | Blondeau et al. |
| 2005/0196571 A1 | 9/2005 | Penny et al. |
| 2006/0000920 A1 | 1/2006 | Leonard |

FOREIGN PATENT DOCUMENTS

| | | |
|---|---|---|
| EP | 1 346 734 | 9/2003 |
| GB | 2254558 A | 10/1992 |
| GB | 3003643 | 11/2002 |
| GB | 3003644 | 6/2003 |
| GB | 3005817 | 7/2003 |
| GB | 3007046 | 9/2003 |
| GB | 3007049 | 9/2003 |
| GB | 3007052 | 9/2003 |
| GB | 3007053 | 9/2003 |
| GB | 3007054 | 9/2003 |
| GB | 3007055 | 9/2003 |
| GB | 3007056 | 9/2003 |
| GB | 3007057 | 9/2003 |
| GB | 3007233 | 9/2003 |
| GB | 3007045 | 10/2003 |
| GB | 3012024 | 2/2004 |
| GB | 3012025 | 2/2004 |
| GB | 3012026 | 2/2004 |
| GB | 3007048 | 10/2005 |
| JP | HA05015803 | 8/1993 |
| JP | 08-241039 | 9/1996 |
| JP | 9-84863 | 3/1997 |
| JP | D1027932 | 9/1998 |
| JP | 10-263068 | 10/1998 |
| JP | D1195937 | 2/2004 |
| NL | 000194709-0001 | 9/2004 |
| NL | 000205661-0001 | 10/2004 |
| NL | 000252358-0001 | 2/2005 |
| NL | 000252366-0001 | 2/2005 |
| WO | WO 9633605 A | 10/1996 |
| WO | WO 00/23121 | 4/2000 |
| WO | WO 03/068276 | 8/2003 |
| WO | WO 2007/096432 | 8/2007 |

OTHER PUBLICATIONS http://www.glade.com/plugins.asp.
http://www.airwick.us/product page/product.html.
http://www.racerwheel.com/tcr-cz-103.html.
http://www.racerwheel.com/tcr-cz-102a.html.
http://www.giftsandgadgetsonline.com/ioairfrwilif.html.
http://www.allproducts.com/gift/sundeal/02-ac105.html.
http://us.shop.com/cc.amos?main=catalog&pcd=783942&adtg=05180436&GA=1.
http://www.autobarn.net/skulrotairfr.html?AID=10274001&PID=613288.
http://www.negativeiongenerators.com/XJ-201ionicfreshener.html.
http://www.buylighting.com/Odor eliminating light bulbs.html.
Int'l Search Report and Written Opinion Appl. No. PCT/US2005/023226 dated Sep. 12, 2005.
International Search Report and Written Opinion in PCT/US2007/008035 dated Aug. 2, 2007.
International Search Report and Written Opinion dated Jun. 29, 2007 for PCT/US2007/001568.

* cited by examiner

AIR FRESHENER WITH FRAME AND REFILL HOLDER

CROSS REFERENCE TO RELATED APPLICATIONS

This application is a continuation-in-part of U.S. patent application Ser. Nos. 10/881,816 and 10/880,885, which were filed on Jun. 30, 2004, now U.S. Pat. No. 7,213,770 and U.S. patent application Ser. No. 11/118,500, which was filed on Apr. 29, 2005. This application claims the benefit to all such previous applications, and such applications are hereby incorporated herein by reference in their entireties.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present invention generally relates to a volatile material dispensing system, and more particularly, to a refillable volatile material dispensing system.

2. Description of the Background

Volatile material dispensing systems have been used to provide fragrances to office or home settings. One such dispenser comprises a holder with a rectangular portion. Two opposing walls extend the length of the rectangular portion and depend from sides thereof. A ridge extends the length of the portion along a center thereof. Inwardly protruding lips extend toward each other from ends of the opposing walls. The area enclosed by the portion, walls, and lips define a slot that can hold a solid material containing a fragrance.

Another dispenser comprises a housing with a rectangular upper portion and a rounded lower portion. A rectangular channel is disposed within the rectangular upper portion. The channel is adapted to receive a solid perfume contained within a rectangular reservoir having a transparent permeable membrane covering one side thereof. A plug is disposed on a rear face of the housing to provide power to a heat conductor for volatizing the solid perfume, a lamp, and an optically sensitive element.

Yet another dispenser comprises a scenting device adapted to function with a heating, air conditioning, or venting system. The device includes a first member that is rectangular in shape and made from an air permeable and relatively porous substance. A frame surrounds the periphery of the member and provides a rigid structure to assist in mounting the device. The device is inserted into a mounting means disposed adjacent an air filter. The mounting means comprises a U-shaped member having an inner groove for slidably receiving the frame therein.

SUMMARY OF THE INVENTION

According to one embodiment of the present invention, a display frame with a refill holder comprises a transparent block having front and rear faces, wherein substantially all of the rear face is exposed to an ambient atmosphere. A U-shaped mounting member is attached to the rear face about an outer periphery of same. The U-shaped mounting member has an inwardly extending wall. A channel is formed in a space between the rear face and the inwardly extending wall. A protrusion is attached to the rear face of the frame, wherein at least one of the protrusion and the inwardly extending wall are configured to distance the rear face from a support surface when the frame is in a substantially horizontal position and provide a substantially unimpeded air passage adjacent the rear face.

According to another embodiment of the present invention, a volatile material dispensing system comprises a reservoir having a first surface and a vapor permeable membrane sealed to an outer periphery of the first surface. A volatile material is contained within the reservoir, wherein the volatile material is diffused through the membrane into an ambient atmosphere. A planar frame has a front face and a rear face, wherein the reservoir is releasably held within a reservoir holder disposed on the rear face of the frame. A protrusion is attached to the rear face of the frame, wherein at least one of the protrusion and the reservoir holder are configured to distance the membrane from a supporting surface when the frame is in a substantially horizontal position providing an air passage sufficient to impede volatile material gases from altering the supporting surface.

According to another embodiment of the present invention, a volatile material dispensing system comprises a reservoir that has a first surface and a vapor permeable membrane sealed to an outer periphery of the first surface. A volatile material is contained within the reservoir, wherein the volatile material is diffused through the membrane into an ambient atmosphere. A planar frame has a front face and a rear face, wherein the reservoir is releasably held within a reservoir holder disposed on the rear face of the frame. The reservoir holder includes a mounting member that extends about a periphery of the rear face and an inwardly directed lip that extends from the mounting member. A protrusion is attached to the rear face of the frame, wherein at least one of the protrusion and the reservoir holder are configured to distance the membrane from a supporting surface when the frame is in a substantially horizontal position providing an air passage sufficient to impede volatile material gases from altering the supporting surface.

BRIEF DESCRIPTION OF THE DRAWINGS

Other aspects and advantages of the present invention will become apparent upon reading the following detailed description and upon reference to the drawings in which.

DETAILED DESCRIPTION OF THE INVENTION

Figure 1:
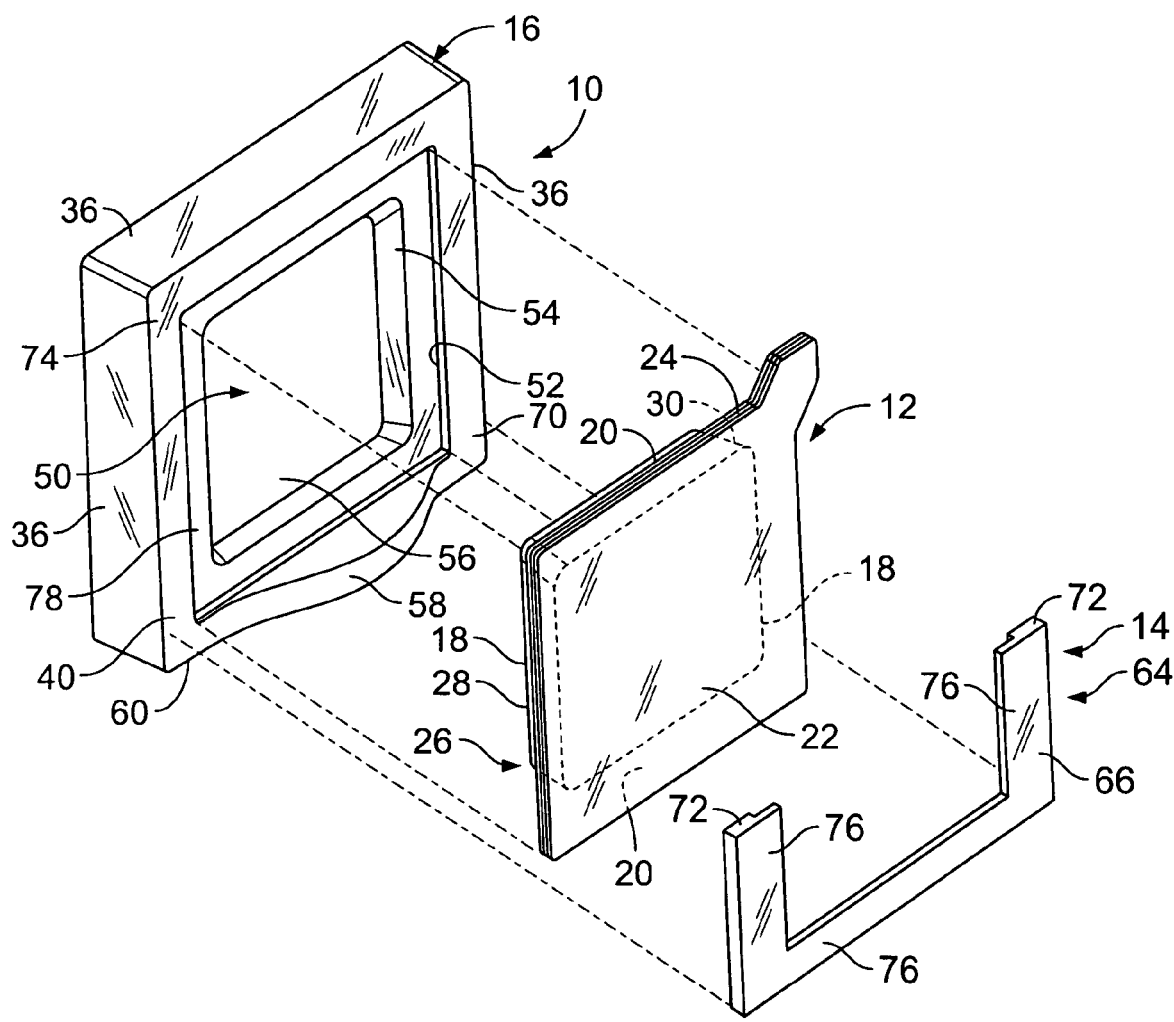
FIG. 1 is an exploded rear isometric view of the volatile material dispensing system that includes a frame, a holder, and a dispenser.
Figure 2:
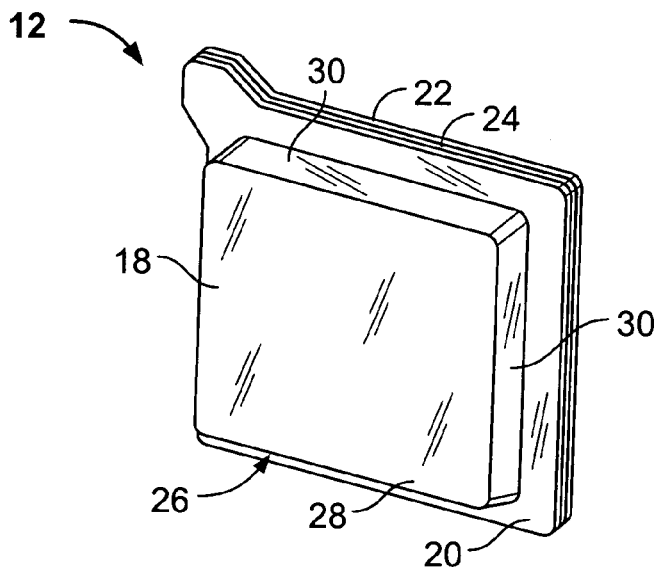
FIG. 2 is an isometric view of the dispenser as shown in FIG. 1.

Referring to FIGS. 1-11, a volatile material dispensing system 10 is illustrated. The dispensing system 10 includes a volatile material dispenser 12, a refillable dispenser holder 14, and a display frame 16. The dispenser 12 is held within the display frame 16 and the dispenser holder 14.

With particular reference to FIGS. 1, 2, 10, and 11, the dispenser 12 includes a blister 18, a peripheral flange 20, and an impermeable laminate 22 releasably adhered to the blister 18 and the flange 20. The blister 18 includes a non-porous permeable membrane 24 and a cup-shaped structure 26. The cup-shaped structure 26 includes a bottom wall 28 and four side walls 30 that in conjunction with the permeable membrane 24 acts as a sealed reservoir to contain a volatile material 32.

Illustratively, the cup-shaped structure 26 is comprised of a recycled polyethylene terephthalate (RPET) layer adhesively bonded to a nylon laminate. The nylon laminate may also include a layer of ethylene vinyl acetate (EVA) coextruded to each side of a middle nylon layer. The nylon laminate and RPET layer of the cup-shaped structure 26 in one embodiment have a thickness of about 0.3 mm (0.012 in.) to about 0.4 mm (0.016 in.). The cup-shaped structure 26 is generally rectangular and/or square with overall dimensions of about 3 mm (0.118 in.) to about 5 mm (0.197 in.) high, about 50 mm (1.969 in.) to about 60 mm (2.362 in.) long, and about 50 mm (1.969 in.) to about 60 mm (2.362 in.) wide. Each cup-shaped structure 26 has four side walls 30. The corresponding side walls 30 each have a height of about 3 mm (0.118 in.) to about 5 mm (0.197 in.) and a width of about 50 mm (1.969 in.) to about 60 mm (2.362 in.). The side walls 30 taper slightly outward as one moves from the bottom wall 28 to the flange 20. The bottom wall 28 is also generally rectangular and has a length of about 48 mm (1.890 in.) to about 58 mm (2.283 in.) and a width of about 48 mm (1.890 in.) to about 58 mm (2.283 in.). The side walls 30 and the bottom wall 28 of the cup-like structure 26 in one embodiment are thermoformed from a single sheet of the RPET and nylon laminate that is heated, then blown and/or pressed into the flange-and-cup arrangement shown in FIG. 2. The cup-shaped structure 26 may be clear and translucent, allowing for the visibility of the volatile material 32 contained within the blister 18. In an alternative embodiment, the cup-shaped structure 26 may be colored and translucent.

The peripheral flange 20 is planar and is coupled to and extends outwardly from top edges of the cup-shaped structure 26. In one embodiment, the peripheral flange 20 extends outwardly from upper edges of the side walls 30. The flange 20 is integrally formed with the cup-shaped structure 26 in, for example, a thermoforming process, as described in the previous paragraph.

Figure 8:
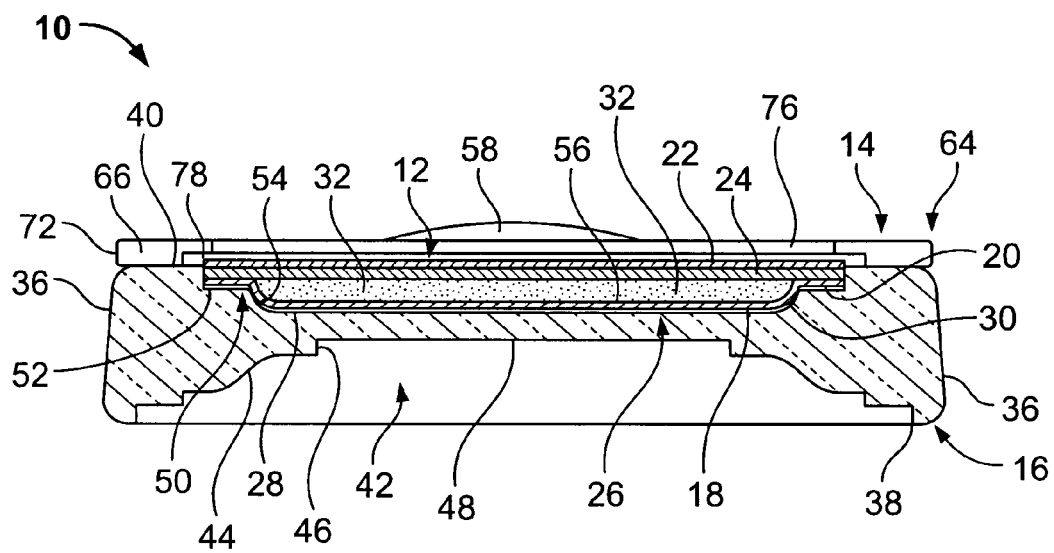
FIG. 8 is a sectional view of the dispensing system taken along the line 8-8 of FIG. 5.
Figure 9:
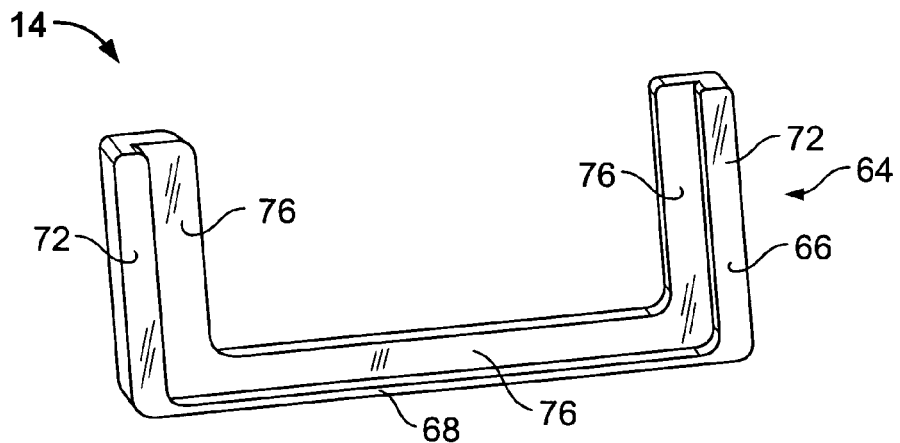
FIG. 9 is an isometric view of the holder of FIG. 1.
Figure 10:
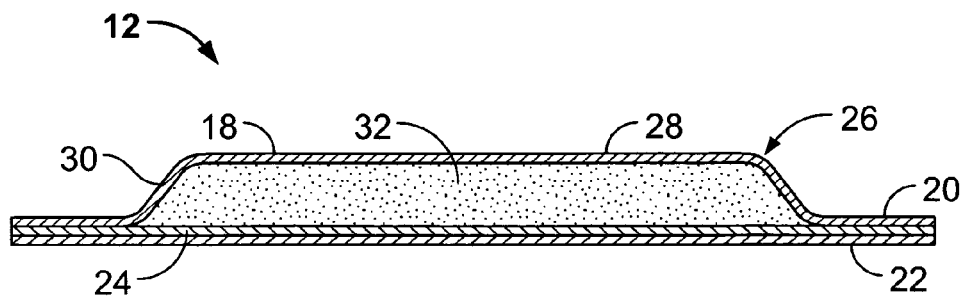
FIG. 10 is a partial enlarged sectional view of the dispenser as shown in FIG. 8 in a filled condition.
Figure 11:
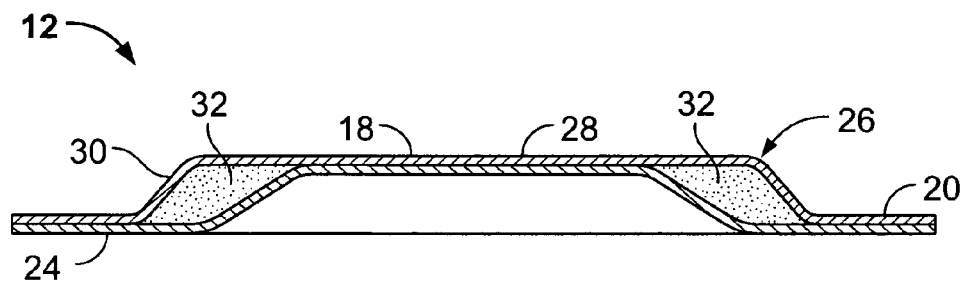
FIG. 11 is a partial enlarged sectional view of the dispenser as shown in FIG. 8 in an unfilled condition.

Illustratively, the permeable membrane 24 has a thickness of about 0.05 mm (0.002 in.) to about 0.15 mm (0.006 in.) and has a density within a range of about 0.88 to 0.95 grams/cubic centimeter. The permeable membrane 24 may also be formed integrally with the impermeable laminate 22 and is heat fused to the flange 20 such that the permeable membrane 24 extends across the entire cup-shaped structure 26. FIGS. 8 and 10 show the permeable membrane 24 and the impermeable laminate 22 enclosing and sealing the cup 26 with the volatile material 32 stored inside, thereby forming a thin sealed container impermeable to the volatile material 32 stored inside. This container remains substantially impermeable until the user grasps a corner of the impermeable laminate 22 and peels the impermeable laminate 22 from the permeable membrane 24, thereby exposing the permeable membrane 24 and permitting the volatile material 32 to migrate through the permeable membrane 24 and diffuse into the ambient air (FIG. 11). The permeable membrane 24 is comprised of low density polyethylene (LDPE) and is clear and translucent, allowing for visibility of the volatile material 32 contained within the blister 18.

The impermeable laminate 22 may include a layer of polypropylene, aluminum foil, and/or polyester. The polypropylene may be adhesively bonded to the aluminum foil layer, which may be adhesively bonded to the polyester layer. An extrusion bonding material may be used to bond the layers together. Illustratively, the impermeable laminate 22 has a thickness of between about 0.1 mm (0.004 in.) and about 0.2 mm (0.008 in.). The polyester layer is generally suitable for printing and may be the outer surface of the impermeable laminate 22.

Following placement of the volatile material 32 into the cup-shaped structure 26, a seal is made between the flange 20 and the permeable membrane 24 thereby forming the dispenser 12. As noted above, the impermeable laminate 22 may be attached to the blister 18 at the same time as the permeable membrane 24 if the impermeable laminate 22 and the permeable membrane 24 are co-extruded. The permeable membrane 24 and the impermeable laminate 22 may be attached to the flange 20 of the blister 18 using any conventional means, such as an adhesive, heat sealing, and/or crimping, or the like. The seal is substantially air-tight so as to prevent leakage of air or the volatile material 32. The volatile material 32 does not completely fill the void within the blister 18. A relatively small amount of air can be tolerated in the dispenser 12 following the creation of the blister 18. For example, the air in the sealed blister 18 is no more than about 3% to about 10% of the overall volume of the blister 18. As the volatile material 32 diffuses out of the dispenser 12 little or no air enters the blister 18 through the permeable membrane 24. In one embodiment, the permeable membrane 24 is configured to distend and collapse with relatively few or no gas bubbles being formed.

There is substantially no diffusion of the volatile material 32 when the dispenser 12 is filled and the impermeable laminate 22 covers the permeable membrane 24. Illustratively, the impermeable laminate 22 is removed from the blister 18 by a user grasping an end of the impermeable laminate 22 and peeling it off the blister 18. A tab 34, extension, or other means for grasping may be included as an extension of the impermeable laminate 22 to aid in removal of same. The extension may be at the corners, ends, and/or on the surface of the impermeable laminate 22.

Following removal of the impermeable laminate 22, the dispensing system 10 begins to transition from a full or first condition (FIGS. 8 and 10) to an empty or second condition (FIG. 11). There may be a small amount of the volatile material 32 that remains in the blister 18 and the dispenser 12 will still be considered to have reached the second condition. As the volatile material 32 diffuses through the permeable membrane 24, the permeable membrane 24 slowly collapses upon the bottom wall 28. With reference to FIG. 11, following diffusion of the volatile material 32 across the permeable membrane 24 there is less volatile material 32 contained within the dispenser 12. Substantially no new air enters the dispenser 12 subsequent to diffusion of the volatile material 32. The result of this is a pressure gradient across the permeable membrane 24, with a higher pressure existing in the ambient air than the pressure in the dispenser 12. The pressure gradient causes the ambient air to exert a net positive pressure upon the dispenser 12, which presses the permeable membrane 24 against the remaining volatile material 32 and ultimately the bottom wall 28. Continued diffusion of the volatile material 32 increases the force exerted upon the permeable membrane 24, which causes the remaining volatile material 32 to migrate from a center of the bottom wall 28 toward a periphery of the bottom wall 28. Continued migration and diffusion of the volatile material 32 results in an increasing surface area contact between the permeable membrane 24 and the bottom wall 28 until the dispenser 12 is empty, or nearly empty. The pressure gradient ultimately resulting in migration of the volatile material 32 may also be viewed as occurring due to an increasing compressed vacuum presence within the dispenser 12 as the volatile material 32 continues to diffuse across the permeable membrane 24.

A small amount of the volatile material 32 may remain within the dispenser 12 when it is nearly empty. The volatile material 32 will typically be present in the form of a ring-like appearance (not shown) toward the periphery of the bottom wall 28. However, in other embodiments the pressure gradient between the ambient air and the interior of the dispenser 12 is reduced, thereby diminishing the tendency of the remaining volatile material 32 to form in a ring-like appearance. In yet other embodiments, the concentration of certain thickening agents imparts a dry crystalline appearance to the remaining volatile material 32. In one embodiment, a dye and a thickener combine to comprise approximately 1% to 3% of the overall volatile material 32 composition of the dispensing system 10 at the first condition. In a different embodiment, the dye and thickener combine to comprise approximately 2% of the overall volatile material 32 composition of the dispensing system 10 at the first condition. A higher composition of dye is present in the volatile material 32 when the dispenser 12 is nearly empty, as the dye utilized does not easily diffuse across the permeable membrane 24. The higher accumulation of dye results in a more readily viewable ring-like appearance. The color of the ring-like image is a more intense color than the coloration of the first condition because of the increased concentration of the dye material. In the second condition the thickener and dye comprise nearly all of the material left within the dispenser 12. Of course, this may change dependent upon the particular dye composition and thickening agent utilized in the volatile material 32.

Figure 3:
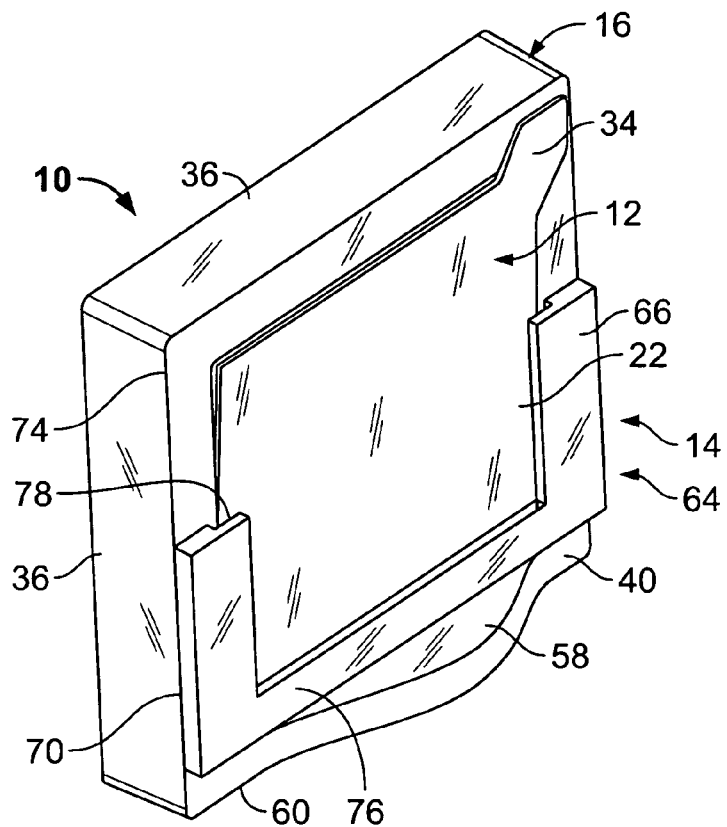
FIG. 3 is a rear isometric view of the assembled dispensing system shown in FIG. 1.
Figure 4:
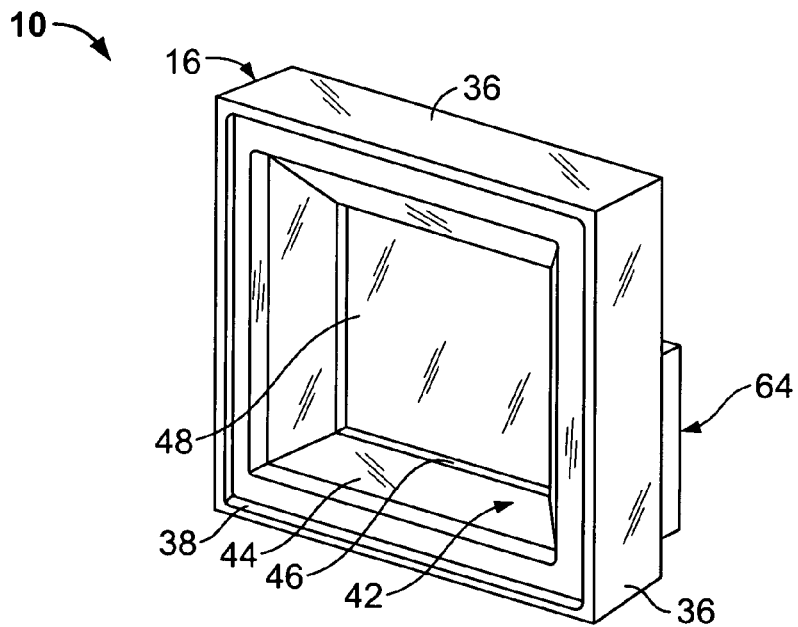
FIG. 4 is a front isometric view of the dispensing system of FIG. 3.
Figure 5:
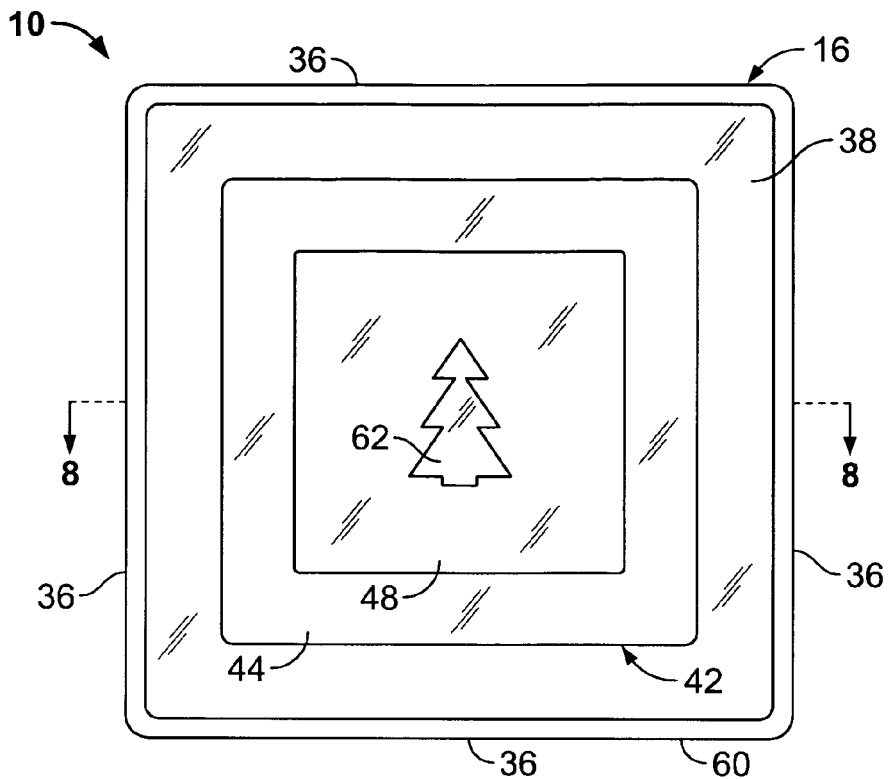
FIG. 5 is a front elevational view of the dispensing system of FIG. 3.
Figure 6:
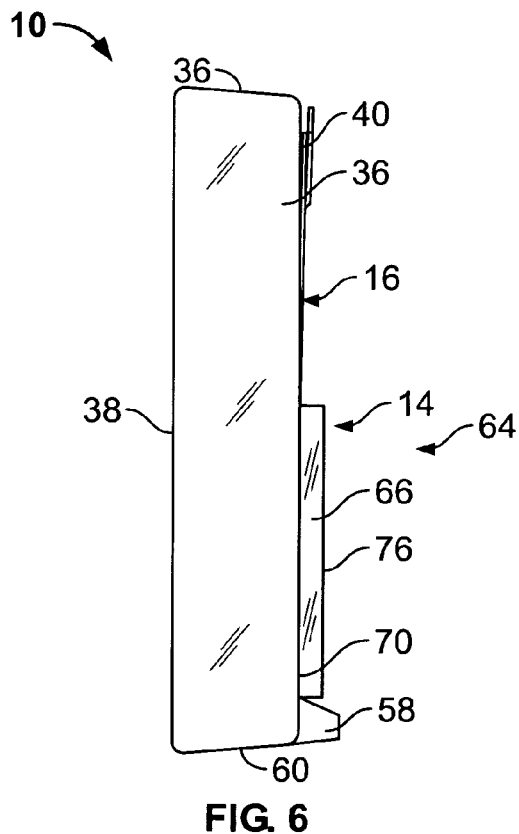
FIG. 6 is a side elevational view of the dispensing system of FIG. 3.

The display frame 16 is a rectangular structure with four substantially equal-sized side walls 36 (FIGS. 1, 3, 4, and 5), a front face 38 (FIGS. 4 and 5), and a rear face 40 (FIGS. 1 and 3). In one embodiment, the display frame 16 has a thickness within a range of about 12 mm (0.472 in.) to about 22 mm (0.866 in.) and a height and width within a range of about 70 mm (2.756 in.) to about 90 mm (3.543 in.). In another embodiment, the display frame 16 has a thickness of about 16 mm (0.630 in.) and a height and width of about 86 mm (3.386 in.). The front face 38 of the display frame 16 in one embodiment has a surface area greater than or equal to about 3000 $mm^2$.

The front face 38 of the display frame 16 includes a recess 42. The recess 42 is defined by recessed ogee-shaped walls 44 and a square depression defined by four side walls 46 and a bottom wall 48. The recess 42 gives the display frame 16 the appearance of a picture frame surrounding and framing the bottom wall 48 of the recess 42. FIG. 8, which shows a cross sectional view of the dispensing system 10, shows the walls 44 and 46 defining the recess 42 with steps and curves in the manner of an ornate picture frame. The recess 42 is centered in the front face 38 and is disposed away from the side walls 36. The front face 38 appears as a border extending around the edges that define the recess 42, wherein the front face 38 has a constant width within a range of about 5 mm (0.197 in.) to about 20 mm (0.787 in.). In a different embodiment, the front face 38 may be planar and devoid of a recess. In yet another embodiment, a single stepped recess is provided. In still another embodiment, a multiple stepped recess is provided. In any of the embodiments described herein, side walls defining the recesses may include curved and/or shaped walls. Further, in any of the embodiments described herein, a raised rib may extend about an outer periphery of the front face 38 adjacent side walls 36 of the display frame 16.

Figure 7:
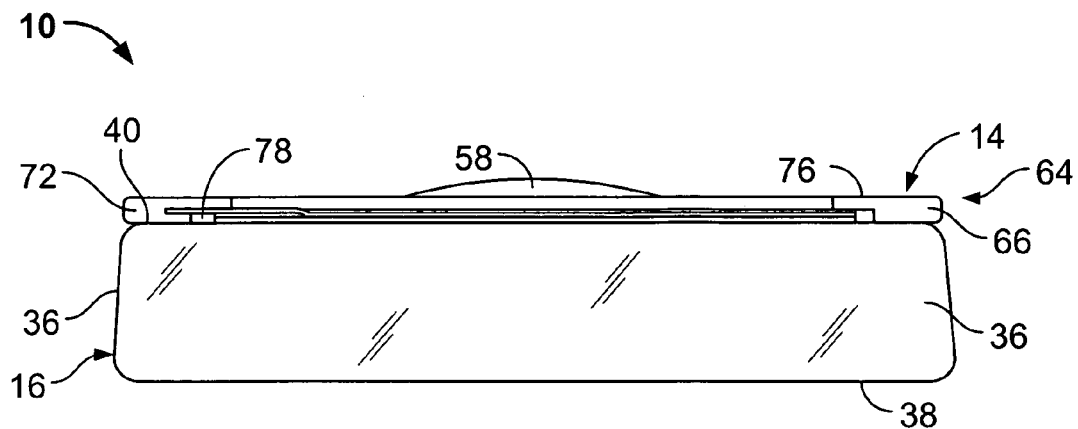
FIG. 7 is a plan view of the dispensing system of FIG. 3.

The rear face 40 of the display frame 16 includes a stepped recess 50 defined by stepped side walls and a square depression disposed therebetween. FIGS. 3, 7, and 8 show that the stepped recess 50 is configured to completely receive the dispenser 12, with dispenser 12 positioned so that the permeable membrane 24 surface is substantially flush with the rear face 40. The stepped recess 50 includes a shallow peripheral recess 52 and a deep central recess 54. The central recess 54 is configured and dimensioned to receive the cup-shaped structure 26, and the peripheral recess 52 is configured and dimensioned to receive and support the flange 20. The central recess 54 and the peripheral recess 52 combined have a negative shape that is the same as that of the dispenser 12.

As may be seen in FIG. 8, the central recess 54 is deeper than the peripheral recess 52 since it accommodates the greater combined thickness of the cup-shaped structure 26, the flange 20, and the permeable membrane 24. The bottom wall 28 of the cup-shaped structure 26 is adjacent to and slightly spaced apart from a bottom 56 of the central recess 54. The central recess 54 and the peripheral recess 52 are centrally spaced from the edges of the rear face 40.

The rear face 40 of the display frame 16 also includes a curved foot 58 disposed adjacent a lower side 60 of the display frame 16. The lower side 60 of the display frame 16 is defined by one of the side walls 36 that rests against a support surface. The curved foot 58 increases the stability of the display frame 16 to prevent same from tipping over. However, should the display frame 16 be tipped over, the curved foot 58 causes the permeable membrane 34 to be spaced from the support surface so that the potential for damage to the support surface by the volatile material 32 is minimized. The curved foot 58 extends outwardly from the rear face 40 about 4 mm (0.157 in.) to about 5 mm (0.197 in.) at its farthest point.

An image 62 is disposed on the rear face 40 of the display frame 16. The image 62 is etched into a central portion of the bottom 56 of the central recess 54. While the present image is a tree, any graphical or textual image may be disposed on the rear face 40. Processes such as printing, forming, molding, etching, or silk screening may be used to place the image 62 onto the rear face 40. In an alternative embodiment, the image 62 may be positioned in any one a plurality of positions on the front face 38, the rear face 40, or the dispenser 12. In yet another embodiment, the image 62 may be absent from the frame dispensing system 10.

The display frame 16 may be constructed from a variety of compositions, including glass or an injection-molded plastic such as a copolyester resin. Illustratively, the display frame 16 is constructed from molded glass that is clear and transparent.

The cup-like structure 26 is therefore viewable through the transparent front face 38. As noted above, the cup-like structure 26 may be clear and translucent, allowing for the visibility of the volatile material 32 contained within the blister 18. In a different embodiment, at least one of the display frame 16 and the cup-like structure 26 is tinted.

FIGS. 1, 3, and 6-9 depict a refill holder 64 for attachment to the rear face 40 of the display frame 16. The refill holder 64 comprises a U-shaped mounting member 66. The U-shaped mounting member 66 is attached to an outer periphery of the rear face 40 and includes a base member 68 that extends lengthwise across a lower portion 70 of the rear face 40. Side members 72 extend upwardly along the periphery of the rear face 40 from the base member 68. The side members 72 extend approximately one-half the distance between the lower portion 70 and an upper portion 74 of the rear face 40. The U-shaped mounting member 66 further includes an inwardly extending wall 76 attached thereto. The inwardly extending wall 76 forms a lip around the U-shaped mounting member 66. A channel 78 is formed in the space between the inwardly extending wall 76 and the rear face 40. More particularly, the channel 78 is formed in the space between the inwardly extending wall 76 and the portion of the rear face 40 defining the peripheral recess 52. The refill holder 64 is attached to the rear face 40 by an adhesive, however, any other type of securing means is considered within the scope of the present disclosure.

The refill holder 64 allows the dispenser 12 to be removed from the display frame 16 and a replacement dispenser (not shown) to be placed into the display frame 16. By way of example, the dispenser 12 of FIG. 3 is removed from the dispensing system 10 by grabbing a portion of the peripheral flange 20 adjacent the upper portion 74 of the display frame 16, or a side wall adjacent the upper portion 74, and pulling the dispenser 12 upwardly and outwardly from the refill holder 64. The channel 78 of the refill holder 64 is sized to be slightly larger than the thickness of the dispenser 12 in an unopened state, i.e., when the impermeable laminate 22 is still releasably adhered to the blister 18 and the flange 20. The extra space in the channel 78 therefore allows a user to pull or otherwise rotate an end of the dispenser 12 adjacent the upper portion 74 outwardly and away from the rear face 40 of the frame 16. Outward movement of the dispenser 12 allows a user to more easily grasp the peripheral flange 20 of the dispenser 12 as opposed to grasping the peripheral flange 20 when it is flush with the rear face 40 of the frame 16. The dispenser 12, or a replacement dispenser (not shown), is placed into the refill holder 64 by grasping an end of the dispenser 12 and orienting the cup-shaped structure 26 toward the rear face 40 of the frame 16. The dispenser 12 is slid downwardly into the channel 78 so that the peripheral flange 20 is disposed between the inwardly extending wall 76 and the shallow peripheral recess 52. Further downward movement of the peripheral flange 20 within the channel 78 forces the cup-shaped structure 26 into the deep central recess 54 and the peripheral flange 20 into the shallow central recess 52. The cup-shaped structure 26 and the peripheral flange 20 are substantially flush with the deep and central recesses 54, 52, respectively, i.e, the cup-shaped structure 26 and the peripheral flange 20 may be completely flush with the portions of the rear face 40 defining the respective recesses 54, 52 or may be spaced wholly or partially therefrom.

The refill holder 64 may also provide a similar benefit as the curved foot 58. Should the display frame 16 be tipped over, the refill holder 64 in combination with the curved foot 58 causes the permeable membrane 34 to be spaced from the support surface so that the potential for damage to the support surface by the volatile material 32 is minimized. In a different embodiment, the refill holder 64 provides the benefit of spacing the permeable membrane 34 from the support surface independent of the curved foot 58. In any of these embodiments, the sizing of the refill holder, i.e., the extent to which the refill holder 64 extends rearwardly from the rear face 40 of the display frame, will determine the effect the refill holder 64 has on minimizing contact between the support surface and the volatile material 32.

Figure 12:
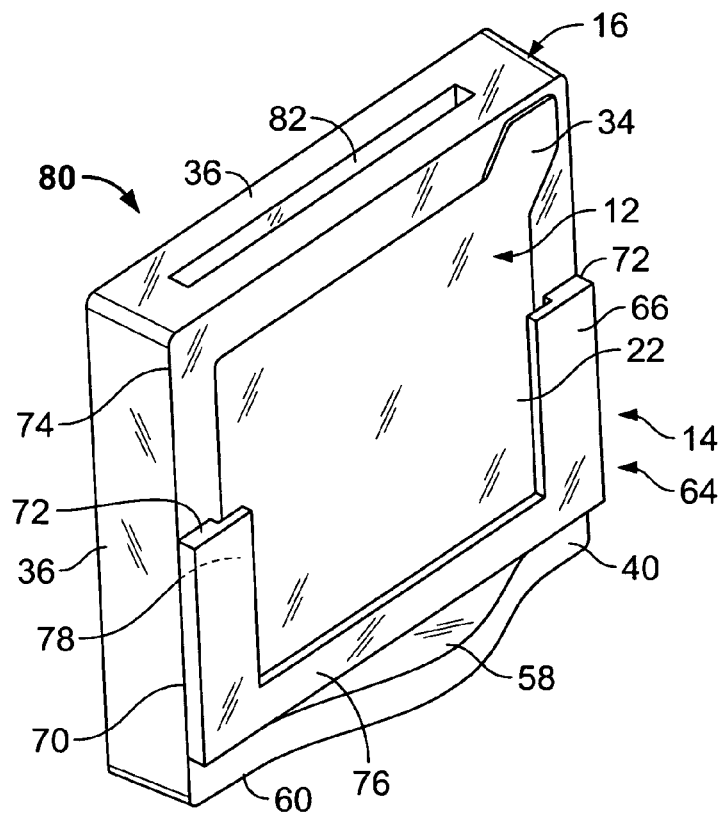
FIG. 12 is a rear isometric view of a dispensing system similar to the one depicted in FIG. 3 with the addition of a slot on a sidewall thereof.

The refill holder 64 is capable of being attached to any type of dispensing system, such as those disclosed in co-pending U.S. patent application Ser. Nos. 10/880,634, 10/881,816, and 10/880,885, which were filed on Jun. 30, 2004, and U.S. patent application Ser. No. 11/118,500, which was filed on Apr. 29, 2005, all of which are incorporated herein by reference in their entireties. For example, application Ser. No. 11/118,500 discloses a dispensing system similar to a dispensing system 80 depicted in FIG. 12. The dispensing system 80 includes a slot 82 for receipt of a picture or other object to be held within the display frame 16 and viewed therethrough. The dispensing system 80 also includes the refill holder 64 for removing and replacing the dispenser 12. One skilled in the art will readily see how the dispensing systems disclosed in the present and above identified applications may be modified to provide for dispenser replaceable dispensing systems.

The refill holder 64 may be made from a similar material as the display frame 16 or a dissimilar material. In the present embodiment, the refill holder 64 comprises a hardened plastic material. The refill holder 64 may also be colored or remain clear to provide certain aesthetic and functional characteristics. In the present embodiment, the refill holder 64 is transparent to allow a user to see through the refill holder 64 and provide a more pleasing appearance. Further, the sizing of the refill holder 64 may be modified to allow the refill holder 64 to be placed onto variously sized frames or to provide for tighter or looser fits of the dispenser 12 within the refill holder 64, e.g., the spacing between the inwardly extending wall 76 and the shallow peripheral recess 52 may be modified or the side members 72 may be lengthened or shortened.

Figure 13:
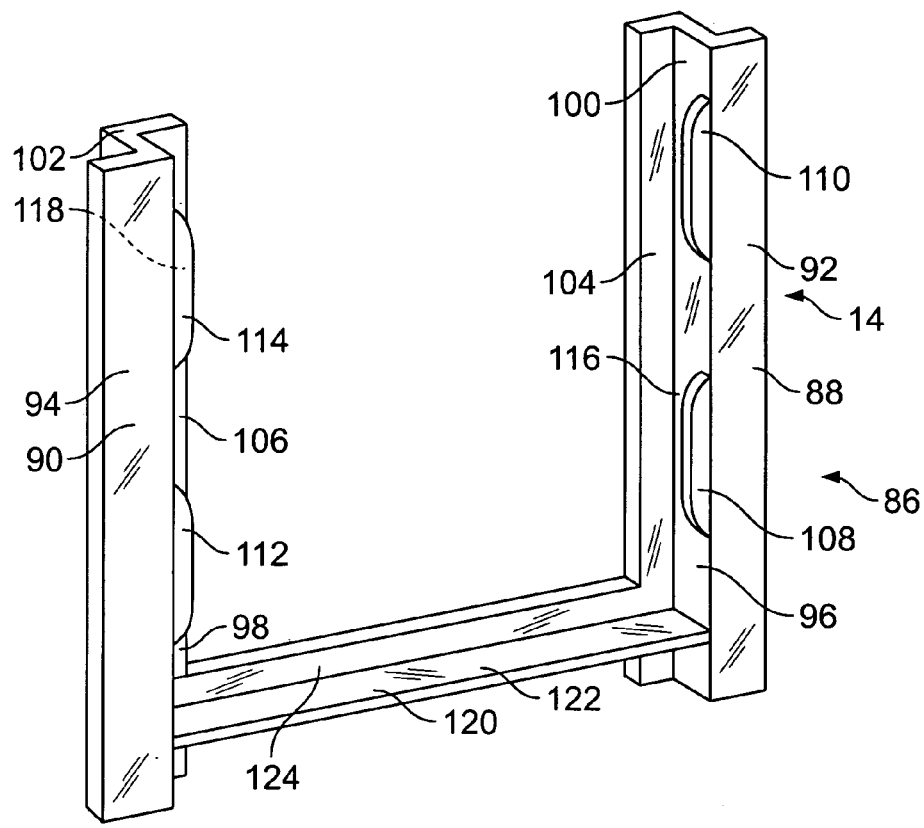
FIG. 13 is an isometric view of a different holder.
Figure 14:
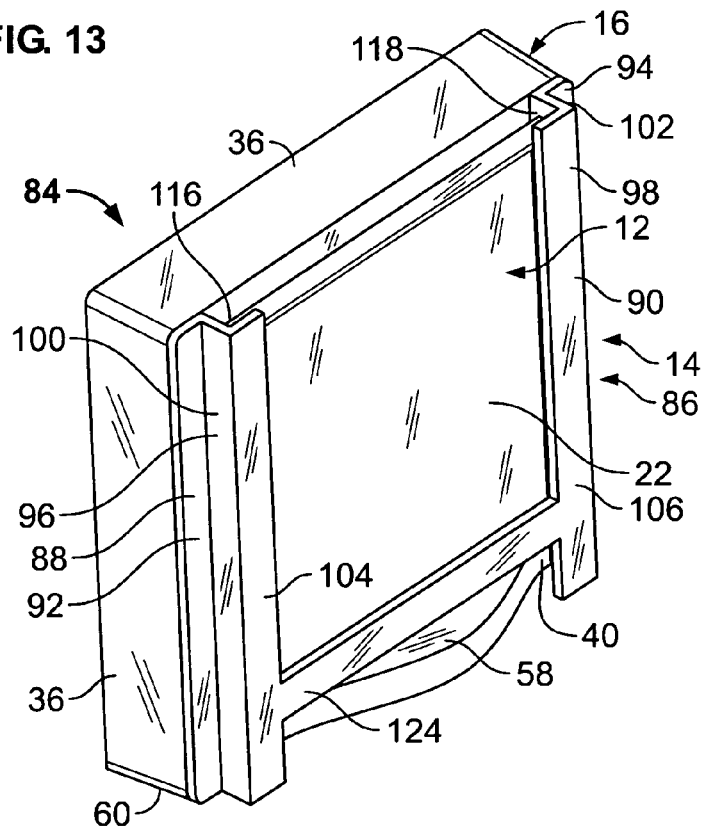
FIG. 14 is a rear isometric view of a dispensing system similar to the one depicted in FIG. 3 with the holder of FIG. 13.

FIGS. 13 and 14 depict a dispensing system 84 with a different refill holder 86 mounted onto the rear face 40 of the display frame 16. The refill holder 86 comprises opposing first and second side members 88, 90, respectively. Each of the first and second side members 88, 90 includes an outwardly extending mounting flange 92, 94, respectively, adhered or otherwise secured to the rear wall 40 of the display frame 16 adjacent a sidewall 36 thereof. First and second L-shaped brackets 96, 98 are integral with the mounting flanges 92, 94, respectively, and extend rearwardly therefrom. Each L-shaped bracket 96, 98 includes a rearwardly extending wall 100, 102 and an inwardly extending wall 104, 106, respectively. First and second tabs 108, 110 are integral with the L-shaped bracket 96 and extend inwardly therefrom toward the opposing side member 90. Third and fourth tabs 112, 114 are likewise integral with the L-shaped bracket 98 and extend inwardly therefrom toward the opposing side member 88. A first channel 116 is formed in a space between the first and second tabs 108, 110 and the inwardly extending wall 104 and a second channel 118 is formed in a space between the third and fourth tabs 112, 114 and the inwardly extending wall 106. A base member 120 is integral with the first and second side members 88, 90 and includes a shelf member 122 and an upwardly extending lip 124.

The refill holder 86 allows the dispenser 12 to be removed from the frame 16 and a replacement dispenser (not shown) to be placed into the frame 16. By way of example, the dispenser 12 of FIG. 14 is removed from the dispensing system 84 by grabbing a portion of the peripheral flange 20 of the dispenser 12 adjacent the upper portion 74 of the display frame 16 and pulling the dispenser 12 upwardly and outwardly from the refill holder 86. The dispenser 12, or a replacement dispenser (not shown), is placed into the refill holder 86 by grasping an end of the dispenser 12 and orienting the cup-shaped structure 26 toward the rear face 40 of the frame 16. The dispenser 12 is slid downwardly into the first and second channels 116, 118 so that the peripheral flange 20 is disposed substantially rigidly therein. The dispenser 12 is fully disposed within the refill holder 86 when one side of the dispenser 12 contacts the shelf member 122 and is disposed between the upwardly extending lip 124 and the rear face 40. Further, when the dispenser 12 is fully disposed within the refill holder 86 the cup-shaped structure 26 does not substantially enter the stepped recess 50. Depending on the sizing of the various components comprising the refill holder 86, the cup-shaped structure 26 may not enter the stepped recess 50 at all.

The refill holder 86 may be attached to any of the dispensing systems disclosed herein or modified accordingly to minimize contact between a support surface and the volatile material 32 when the display frame 16 is tipped over. Further, the refill holder 86 may be constructed of any of the materials and/or colored according to the disclosure herein. Still further, any modifications disclosed herein may similarly be made to the present refill holder 86. For example, the sizing of the refill holder 86 may be adjusted to accommodate variously sized dispensing systems, to provide a tighter or looser fit within the first and second channels 116, 118, to lengthen or shorten the first and second side members 88, 90, or to space the rear face 40 of the display frame 16 from a support surface should the display frame 16 tip over. Yet another non-exclusive modification of the refill holder 86 comprises the provision of differently shaped or positioned tabs 108, 110, 112, 114. Further, the number of tabs may be increased or decreased so as to have an equal or unequal number of tabs on opposing side members 88, 90.

INDUSTRIAL APPLICABILITY

The volatile material dispensing system described herein advantageously provides a refillable fragrance dispenser. Thus, a user may easily replace a depleted fragrance dispenser as opposed to discarding the entire dispensing system.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A display frame with refill holder, comprising:
   a transparent block having front and rear faces, wherein substantially all of the rear face is exposed to an ambient atmosphere;
   a U-shaped mounting member attached to the rear face about an outer periphery of same, the U-shaped mounting member having an inwardly extending wall, wherein a channel is formed in a space between the rear face and the inwardly extending wall; and
   a protrusion attached to the rear face of the frame, wherein at least one of the protrusion and the inwardly extending wall are configured to distance the rear face from a support surface when the frame is in a substantially horizontal position and provide a substantially unimpeded air passage adjacent the rear face.

2. The display frame of claim 1, wherein a stepped recess is disposed within the rear face, the stepped recess including a peripheral recess and a central recess.

3. The display frame of claim 2, wherein the channel is defined by the space between the portion of the rear wall defining the peripheral recess and the inwardly extending wall.

4. The display frame of claim 3, wherein a fragrance dispenser comprising a blister and a peripheral flange extending thereabout is replaceably inserted into the U-shaped mounting member.

5. The display frame of claim 4, wherein the peripheral flange is held within the channel so that the peripheral flange is substantially flush with a portion of the rear wall defining the peripheral recess and a bottom end of the blister is substantially flush with a portion of the rear wall defining the central recess.

6. The display frame of claim 1, wherein at least one of the U-shaped mounting member and the inwardly extending wall comprises a transparent material.

7. The display frame of claim 1, wherein the U-shaped mounting member and the inwardly extending wall are comprised of a different material than the display frame.

8. The display frame of claim 1, wherein the U-shaped mounting member and the inwardly extending wall provide means for replaceably holding a fragrance dispenser.

9. A volatile material dispensing system, comprising:
   a reservoir having a first surface and a vapor permeable membrane sealed to an outer periphery of the first surface;
   a volatile material contained within the reservoir, wherein the volatile material is diffused through the membrane into an ambient atmosphere;
   a planar frame having a front face and a rear face, wherein the reservoir is releasably held within a reservoir holder disposed on the rear face of the frame; and
   a protrusion attached to the rear face of the frame, wherein at least one of the protrusion and the reservoir holder are configured to distance the membrane from a supporting surface when the frame is in a substantially horizontal position providing an air passage sufficient to impede volatile material gases from altering the supporting surface.

10. The system of claim 9, wherein the rear face of the frame includes a stepped recess having an inner and an outer recess.

11. The system of claim 10, wherein the inner recess is deeper than the outer recess, and wherein the inner recess and the outer recess are adapted to hold a cup-like structure of the reservoir and the outer periphery of the first surface of the reservoir, respectively.

12. The system of claim 9, wherein the reservoir holder comprises opposing first and second side members secured to the rear face adjacent side walls of the frame and a base member extending between the first and second side members adjacent a lower portion of the frame.

13. The system of claim 12, wherein each of the first and second side members includes a mounting flange secured to the rear face of the frame, an L-shaped bracket having walls that extends rearwardly and inwardly from the mounting flange, and at least one tab extending inwardly from the L-shaped bracket.

14. The system of claim 13, wherein each of the first and second side members includes a channel formed in a space between the inwardly extending wall of the L-shaped bracket and the at least one tab, wherein the channel is adapted to allow the outer periphery of the first surface of the reservoir to fit therein.

15. The system according to claim 9, wherein the system further comprises a removable vapor impermeable laminate covering the vapor permeable membrane to prevent diffusion of the volatile material.

16. The system according to claim 9, wherein the volatile material comprises at least one of an air freshener, fragrance, insecticide, insect repellent, odor eliminator, aromatherapeutic material, sanitizer, and mold or mildew inhibitor.

17. A volatile material dispensing system, comprising:
- a reservoir having a first surface and a vapor permeable membrane sealed to an outer periphery of the first surface;
- a volatile material contained within the reservoir, wherein the volatile material is diffused through the membrane into an ambient atmosphere;
- a planar frame having a front face and a rear face, wherein the reservoir is releasably held within a reservoir holder disposed on the rear face of the frame, and wherein the reservoir holder comprises a mounting member extending about a periphery of the rear face and an inwardly directed lip extending from the mounting member; and
- a protrusion attached to the rear face of the frame, wherein at least one of the protrusion and the reservoir holder are configured to distance the membrane from a supporting surface when the frame is in a substantially horizontal position providing an air passage sufficient to impede volatile material gases from altering the supporting surface.

18. The system of claim 17 further including a slot disposed in the planar frame, which is configured to hold an image.

19. The system of claim 17, wherein a channel is formed in the space between the lip and the rear face of the frame, the channel being adapted to allow the outer periphery of the first surface of the reservoir to fit therein.

20. The system of claim 18, wherein the image comprises at least one of a photograph, picture, and drawing.

* * * * *